United States Patent [19]
Groff et al.

[11] Patent Number: 6,102,856
[45] Date of Patent: Aug. 15, 2000

[54] WEARABLE VITAL SIGN MONITORING SYSTEM

[76] Inventors: Clarence P Groff, 231 N. Woodlake, Columbia, S.C. 29223; Paul L Mulvaney, 333 White Hurst Way, Columbia, S.C. 29229

[21] Appl. No.: 09/022,422

[22] Filed: Feb. 12, 1998

Related U.S. Application Data

[60] Provisional application No. 60/039,721, Feb. 12, 1997.

[51] Int. Cl.$^7$ .............................. A61B 5/00; G08B 23/00
[52] U.S. Cl. .......................... 600/301; 128/903; 340/573
[58] Field of Search ................... 600/300, 301; 340/573; 128/920, 903, 904

[56] References Cited

U.S. PATENT DOCUMENTS

| | | | |
|---|---|---|---|
| 4,090,504 | 5/1978 | Nathan ................................... | 600/483 |
| 4,343,315 | 8/1982 | O'Leary .................................. | 600/502 |
| 4,457,315 | 7/1984 | Bennish ................................. | 600/517 |
| 4,503,859 | 3/1985 | Petty et al. ............................. | 600/350 |
| 4,705,048 | 11/1987 | Pfohl et al. ............................. | 600/528 |
| 4,763,663 | 8/1988 | Uphold et al. .......................... | 600/484 |
| 4,889,132 | 12/1989 | Hutcheson et al. .................... | 600/493 |
| 4,974,601 | 12/1990 | Tranjan et al. ......................... | 600/509 |
| 5,010,890 | 4/1991 | Pfohl et al. ............................. | 600/528 |
| 5,261,401 | 11/1993 | Baker et al. ............................ | 607/9 |
| 5,365,935 | 11/1994 | Righter et al. ......................... | 600/523 |
| 5,375,604 | 12/1994 | Kelly et al. ............................. | 600/484 |
| 5,462,051 | 10/1995 | Oka et al. ............................... | 600/300 |
| 5,522,396 | 6/1996 | Langer et al. .......................... | 600/509 |
| 5,652,570 | 7/1997 | Lepkofker .............................. | 600/301 |
| 5,704,364 | 1/1998 | Saltzstein et al. ...................... | 600/300 |
| 5,772,586 | 6/1998 | Heinonen et al. ...................... | 600/300 |

*Primary Examiner*—Cary O'Connor
*Assistant Examiner*—Navin Natnithithadha
*Attorney, Agent, or Firm*—Michael A Mann; Nexsen Pruet Jacobs and Pollard

[57] ABSTRACT

The present invention is a wearable vital sign monitor. The device is worn preferably about the chest just below the pectoral muscles and monitors at least the following: ECG data, respiration rate, oxygen uptake, pulse rate, and body temperature. These data are collected and analyzed to determine if there is a deviation from the wearer's normal condition, which the device learns. If there is, the device sends a signal to a remote central facility to be received by an attendant who is capable of ascertaining whether the abnormal condition is in fact a warning sign of an adverse health condition. If necessary, the attendant can communicate by voice with the wearer. Optionally, the attendant can locate the wearer, assuming that the wearer is unable to speak, using a ground positioning satellite (GPS) locating system. Finally, the device is capable of producing periodic reports of the recorded data.

19 Claims, 2 Drawing Sheets

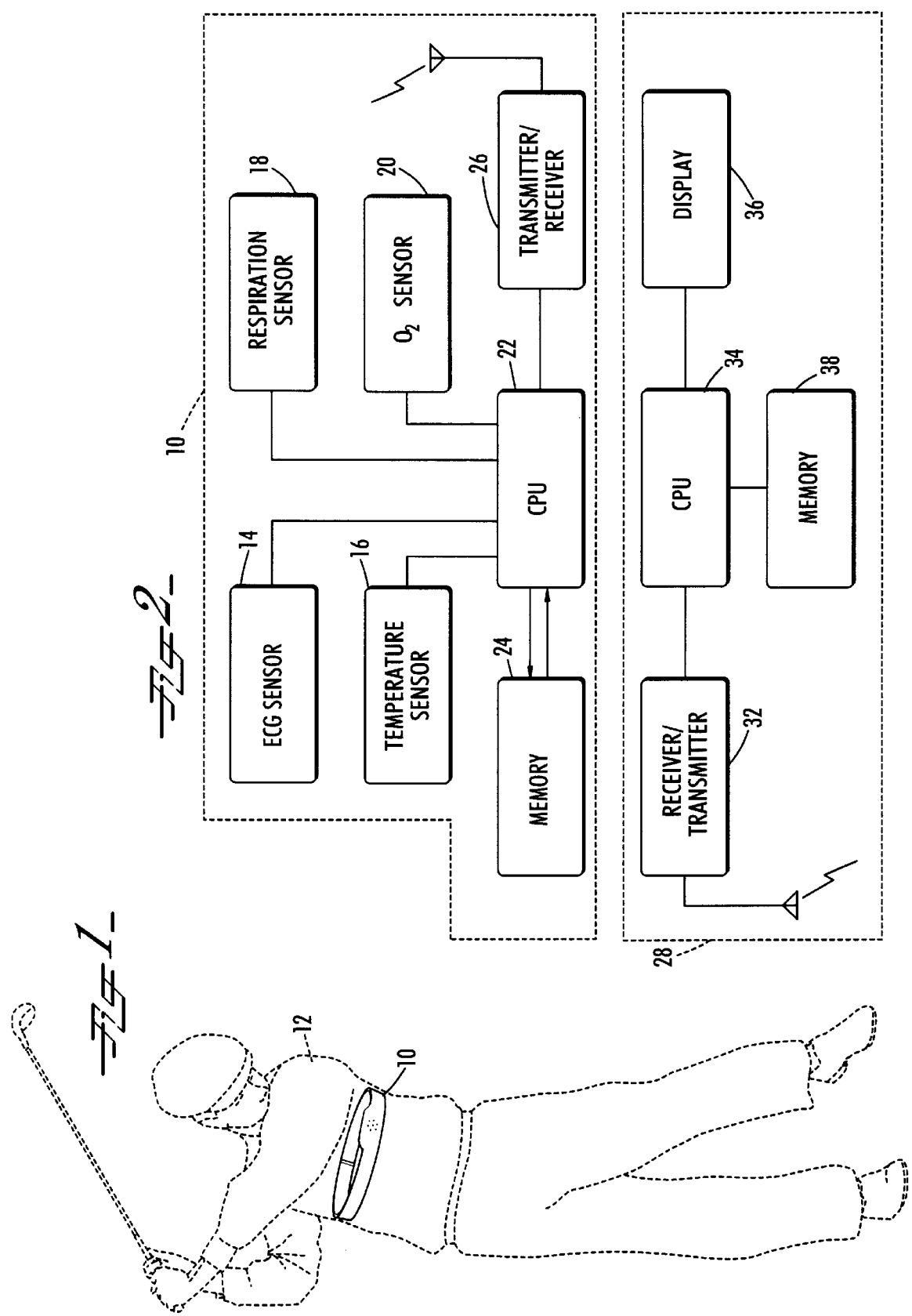

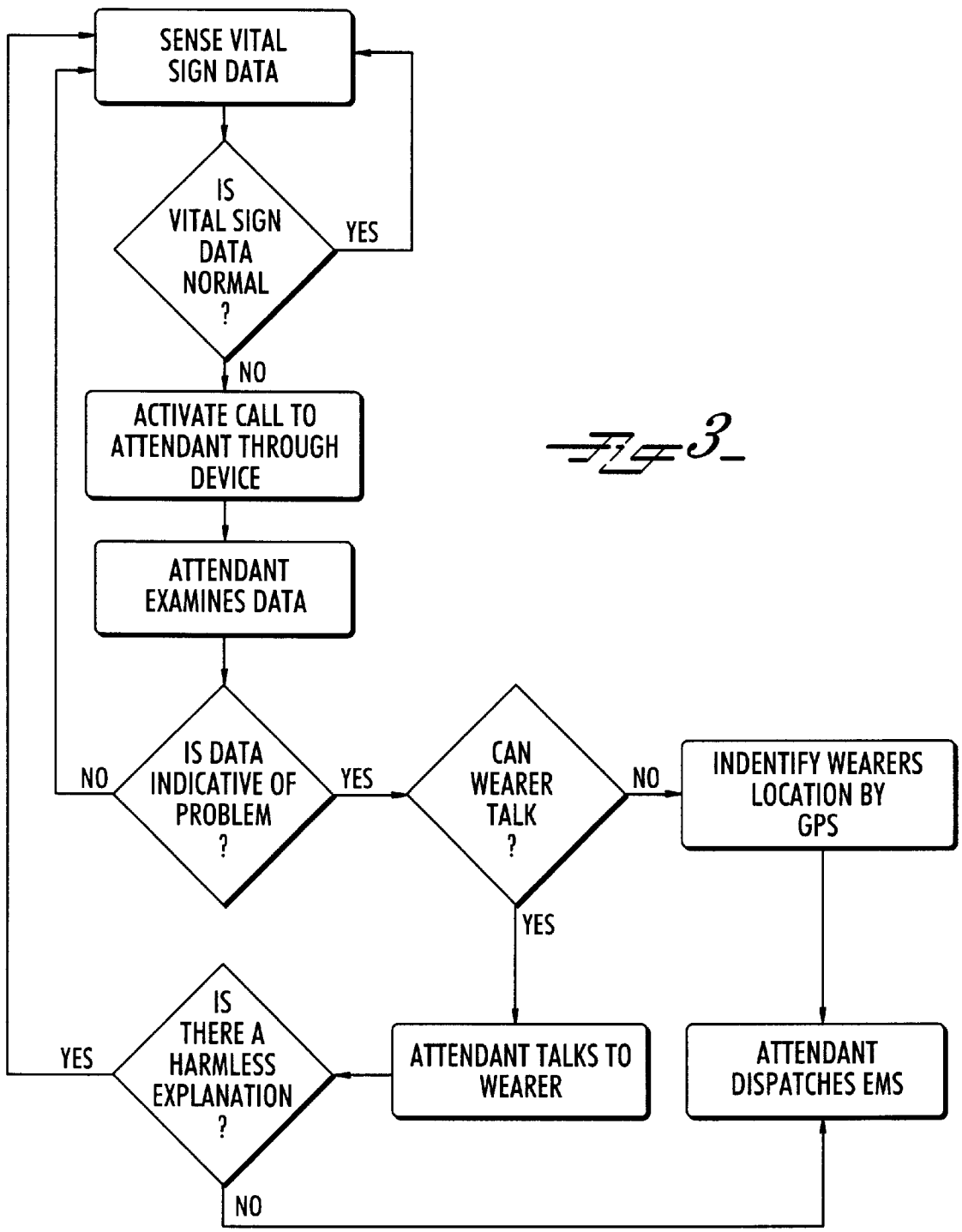

WEARABLE VITAL SIGN MONITORING SYSTEM

The applicant claims the benefit of the priority of its provisional patent application filed Feb. 12, 1997, Ser. No. 60/039,721.

BACKGROUND OF THE INVENTION

1. Field of the Invention

The present invention relates generally to monitoring vital signs and in particular to wearable or portable monitors.

2. Discussion of Background

A high proportion of the human population has a significant risk for heart disease. Heart disease is the leading killer in western society and is a significant component of medical costs. Avoiding heart disease involves identification of who is at risk and then taking the appropriate steps to reduce that risk. To identify who is at risk, most people simply get by with an occasional physical examination to determine the extent to which they are at risk or if their risk factor has changed for the worse. Others, however, would benefit by more frequent evaluation of their major vital signs, especially if their risk factors cannot be reduced. Vital signs include body temperature, electrocardiographic data, blood pressure, heart rate, respiration rate, and oxymetry data.

There are a number of monitors that are known and being sold commercially. Most of these detect and record the heartbeat of the wearer over an interval; some also analyze it to determine if the heartbeat is in some way abnormal. Those that record heartbeat have the capability of transferring the recorded data to a computer for analysis and evaluation, perhaps by direct electrical connection to a computer or perhaps by transmission over a telephone line.

Kelly, et al. in U.S. Pat. No. 5,375,604, teach a portable device for monitoring vital signs of a patient. The device is intended for bedside use in a hospital and monitors electrocardiogram signals, body temperature, blood pressure, respiration, pulse and other parameters. Additionally, the device includes a communications capability to a local area network when the monitor is placed in a docking station.

In U.S. Pat. No. 5,365,935, Righter, et al. teach an even more portable monitoring device in the form of a watch for monitoring ECG signals by an individual who is not in a hospital. In one embodiment, a modem can be attached to the device for burst mode transmission to a receiver at a doctor's office or other remote location.

Baker, et al. describe a heart monitor in U.S. Pat. No. 5,261,401, worn by an individual known to have a heart condition and who is fitted with a pacemaker. The device communicates electrically with the user's pacemaker to cause the latter to respond to the wearer's needs.

In another wearable monitor disclosed by Hutcheson, et al. in U.S. Pat. No. 4,889,132, data related to heart rate and pulse can be transmitted via a modem for display on, for example, a computer. The blood pressure is determined by inflating a cuff worn by the individual.

Finally, in U.S. Pat. No. 4,974,601, Tranjan, et al. disclose a portable heart monitor that compares the sensed heartbeat with normal heart wave forms to identify erratic ones and provide real-time warning of the erratic heartbeats. A warning signal of an erratic heartbeat is given.

However, there appear to be no known devices that are worn by a user and that both sense data related to the wearer's vital signs and report anomalous data immediately to those who diagnose anomalous vital signs so that assistance can be provided as soon as possible if necessary. There remains, therefore, a need for improvements in vital sign monitoring systems.

SUMMARY OF THE INVENTION

According to its major aspects and briefly described, the present invention is a vital sign monitoring system. The system comprises a wearable monitoring unit and a central station with which each unit communicates. The unit is worn on the body in engagement with the skin at a location where data relevant to vital signs can be accurately sensed, such as about the chest just below the pectoral muscles. The unit collects some or all of the following: body temperature data, electrocardiographic data, respiration data, and oxymetry data. These data are collected, stored and analyzed to detect if there is a deviation from the wearer's normal condition, which the device is programmed to learn. If there is, the device initiates a signal to a remote central facility where an attendant is on duty and is capable of ascertaining whether the anomalous condition is in fact a warning sign of an adverse health condition such as the onset of a heart attack. If necessary, the attendant can communicate by voice directly with the wearer using a dedicated "telephone" incorporated into the unit. Optionally, if the wearer requires intervention by emergency health professionals and is incapable of communicating his location, the attendant can locate ground position of the wearer using a ground positioning satellite (GPS) locating system.

An important feature of the present invention is the ability to communicate by voice between the attendant and the wearer. This feature is important for two reasons. Pure data cannot always be accurately analyzed out of context and by communicating with the wearer, the cause of the anomalous data can be ascertained. The cause may have nothing to do with the wearer's health. However, if the wearer is having a health-related problem, he may be kept calm by speaking to someone who can advise him as to what to do until help arrives, thus preventing panic or an inappropriate response by the wearer.

Another significant feature of the present invention is the optional inclusion of the ability to pinpoint the location of the wearer by using GPS. The wearer may not be capable of talking, may not know exactly where he is, or may be mistaken about where he is. This feature prevents costly loss of time searching for the wearer. The combination of the two-way voice mode of operation and location determination enable the wearer to enjoy greater flexibility of activities and movement while providing the security that, in the event of a health emergency, assistance will be forthcoming.

Other features and their advantages will be apparent to those skilled in the art of vital sign monitoring devices from a careful reading of the Detailed Description of Preferred Embodiments accompanied by the following Drawings.

BRIEF DESCRIPTION OF THE DRAWINGS

In the drawings,

FIG. 1 is a perspective view of a device worn by an individual, according to a preferred embodiment of the present invention;

FIG. 2 is a schematic view of a device according to a preferred embodiment of the present invention; and FIG. 3 is a flow chart of the method of operation of a device when operating according to a preferred embodiment of the present invention.

DETAILED DESCRIPTION OF PREFERRED EMBODIMENTS

The present invention is a vital sign monitoring system. The system comprises two major components: a wearable unit having a plurality of sensors for continually sensing vital signs and analyzing them, and a central facility in communication with each unit and its wearer. One facility can service many units, depending on staffing and other capabilities. Data from the wearable unit flows to the central facility when the data being sensed by the unit indicate that the wearer may be suffering from the onset of an anomalous condition, as indicated by vital sign data. Voice mode permits an attendant at the facility to determine by speaking to the wearer whether or not he is in danger and requires intervention by medical personnel.

Referring now to the figures, FIG. 1 shows the wearable unit 10 worn by an individual 12. Unit 10 encircles the chest just below the arms and pectoral muscles, where it will not interfere with arm movement but can be placed in contact with the skin and will be just over the ribcage. The wearable unit is preferably very flexible and comfortable and adjustable or stretchable so that it can be made to fit the wearer snuggly. The present unit is intended not only for those who are at high risk for a heart attack or other potentially fatal health condition, but also for those who wish to monitor their vital signs simply for personal reasons or who are engaging in particularly strenuous activity.

Wearable unit 10 is thin and lightweight to as to be reasonably comfortable to the wearer, to fit easily under clothing, and to not interfere with the wearer's normal activities. It continuously and passively senses data related to the major vital signs and analyzes them to determine if the data is anomalous for that wearer. The vital signs monitored include some or all of the following: body temperature, electrocardiographic (ECG) data, oxymetry data, pulse, and respiration rate. Other data may be sensed and the device may be tailored to the health needs of a particular individual.

Unit 10 routinely collects and stores data from four sensors: ECG sensor 14, a temperature sensor 16, a respiration sensor 18, and a oxygen sensor 20 (FIG. 2). These are fed to a central processing unit 22 where they are stored in memory 24 and transmitted by a transmitter 26 from unit 10 to central facility 28 when anomalous data is sensed. Optionally, summary data can also be transmitted daily or at other time intervals by unit 10 for reports.

The sensed data is stored in memory 24 so that unit 10 can learn the normal condition of its wearer. After collecting only a few minutes' worth of data, each sensor will provide output from which a nominal range or pattern can be determined; that is, a representative heartbeat, a temperature range, a respiration rate range, and representative oxymetry data can be established. This nominal range will be updated as additional data is received. In this way, central processor 22 can both "learn" the ranges and patterns of vital signs of its wearer and be on the lookout for anomalous data. Anomalous data is defined statistically by, for example, the data being more than one standard deviation from the nominal range or pattern.

If wearable unit 10 senses anomalous data rather than what would be normal data for the individual (see FIG. 3), its central processing unit 22 initiates a call via a transmitter 26 such as a cellular telephone or 900 MHz cordless telephone that is incorporated into unit 10 to a receiver 32 at central facility 28. The received data is put onto a display 36 by a central processing unit 34 there for review and analysis by an attendant and into a memory 38 for storage. The attendant is trained to evaluate the data to determine if (1) there is no problem, (2) there is a problem, and (3) a higher level of expertise is required to determine whether there is a problem or not. An attendant is available to evaluate incoming anomalous data twenty-four hours a day, seven days a week.

To help in assessing the data, the attendant can communicate by voice with the wearer via a "telephone" incorporated into unit 10. The telephone is incorporated into the wearable unit and is dedicated to communications between the wearer and the central facility. It may be that a simple explanation by the wearer can clarify the anomalous data. However, in the event the wearer is not able to speak or is incoherent and the data indicates that there is a problem, the attendant can locate the wearer because of a built-in locating system based on satellite positioning. Remotely, the attendant can cause unit 10 to transmit its exact location to central facility 28. The attendant can then dispatch emergency medical services personnel to the wearer's location.

The wearable unit incorporates technology that, while state of the art, does not include any major component that itself is new. The various sensors, cellular or cordless telephone, and satellite position locating system are all known and available from one or more manufacturers. The cellular telephone need not have the capability to dial numbers or display numbers called as do conventional cellular telephones, so its size is considerably reduced. Similarly, sensors for sensing and outputting the various data are also well known and of small size. For example, body temperature sensor 16 is based on a thermocouple in contact with the skin. Respiration sensor 18 is based on a strain gauge built into unit 10. Oxygen sensor 20 is based on photometry, using light reflected by the skin to assess its oxygen content by the intensity and wavelengths of the light they absorb and reflect. Alternatively, respiration and oxymetry information may be sensed or inferred from data regarding the impedence of the skin. ECG data is based on technology similar to that disclosed by Righter, et al. in U.S. Pat. No. 5,365,935. Pulse data is inferred by a standard mathematical algorithm from the ECG data. Transmission and receipt of data can be, as indicated above, by cellular or cordless telephone in either voice mode or data mode. The data can be compressed by central processing unit 22 and decompressed by central processing unit 34 and transmitted in a burst or continuously. Voice mode can take place simultaneously with data mode by multiplexing the signals or by digitizing voice and sending it at a different frequency.

As technology develops, other indicators of health can be added to the present device either for a more complete picture of the wearer's health, for corroboration of other data received, or for sensing particular conditions of the wearer such as insulin shock or epileptic seizures.

Anomalous or summary data from the sensors is output for collection, storage in memory 38 and transmission to central facility 28 for preparation of reports. Analysis of the data to determine if, compared to that particular wearer's normal condition, there is an anomalous condition, will be done by the central processing unit 22 carried by wearable unit 10 so that, if such a condition appears to exist, it can initiate contact with the central station. Alternatively or additionally, the analysis can be done at central station 28 by its CPU 34, and if there is anomalous data, the attendant can call the wearer.

It will be apparent to those skilled in the art of vital sign monitors that many changes and substitutions can be made to the foregoing preferred embodiments without departing from the spirit and scope of the present invention.

What is claimed is:

1. A vital sign monitoring system, comprising:
 a skin-engaging unit carrying
  vital sign sensor means for acquiring vital sign data about a user\said vital sign sensor means having an output, and means responsive to said output of said vital sign sensor means for collecting and storing said vital sign data, means in operative connection with said collecting and storing means for analyzing said vital sign data to detect anomalous vital sign conditions, wherein said analyzing means detects normal vital sign conditions from statistical analysis of vital sign data, means for transmitting signals from said unit when anomalous vital sign conditions are detected by said analyzing means, and means for receiving voice signals transmitted to said unit.

2. The vital sign monitoring system as recited in claim 1, further comprising means for locating the ground position of said unit, said transmitting means transmitting said ground position from said unit.

3. The vital sign monitoring system as recited in claim 1, wherein said transmitting means can transmit in voice and data mode from said unit.

4. The vital sign monitoring system as recited in claim 1, wherein said skin engaging unit is adapted to encircle the chest of a user.

5. The vital sign monitoring system as recited in claim 1, wherein said vital sign sensor means is selected from the group consisting of an electrocardiogram sensor, a respiratory sensor, an oxymetry sensor, and combinations thereof.

6. The vital sign monitoring system as recited in claim 1, wherein said transmitting means transmits data summaries of vital sign data from said unit.

7. A vital sign monitoring system, comprising:

a central facility having a receiver and a transmitter; and a skin-engaging unit remote from said central facility and carrying vital sign sensor means for acquiring vital sign data from a user said vital sign sensor means producing an output, and means responsive to said output of said vital sign sensor means for collecting and storing said vital sign data, means in operative connection with said collecting and storing means for analyzing said vital sign data to detect anomalous vital sign conditions and normal vital sign conditions, wherein said analyzing means determines normal and anomalous vital sign conditions from statistical analysis of vital sign data, transmitter for transmitting signals from said unit to said receiver of said central facility, said transmitter transmitting said signals when anomalous vital sign conditions are detected by said analyzing means; and receiver for receiving voice signals transmitted to said unit from said transmitter of said central facility.

8. The vital sign monitoring system as recited in claim 7, further comprising means for locating the ground position of said unit.

9. The vital sign monitoring system as recited in claim 7, wherein said transmitting means can transmit in voice and data mode.

10. The vital sign monitoring system as recited in claim 7, wherein said anomalous vital sign conditions are vital sign data that exceed by at least one standard deviation vital sign data of normal vital sign conditions.

11. The vital sign monitoring system as recited in claim 7, wherein said skin engaging unit is adapted to encircle the chest of a user.

12. The vital sign monitoring system as recited in claim 7, wherein said vital sign sensor means is selected from the group consisting of a temperature sensor, an electrocardiogram sensor, a respiratory sensor, an oxymetry sensor, and combinations thereof.

13. The vital sign monitoring system as recited in claim 7, wherein said transmitter of said unit transmits data summaries from said unit to said receiver at said central facility.

14. The vital sign monitoring system as recited in claim 7, wherein said receiver and transmitter of said unit are a cellular telephone having voice mode so that said user can talk to said central facility.

15. The vital sign monitoring system as recited in claim 7, wherein said receiver and transmitter of said unit are a cellular telephone having voice mode and data mode so that said user can talk to said central facility and said unit can transmit vital sign data.

16. A method for monitoring vital signs, said method comprising the steps of:

sensing vital sign data of an individual;

collecting and storing said vital sign data;

analyzing said collected and stored data to detect nominal an anomalous vital sign conditions;

transmitting a signal to a remote central facility in the event an anomalous vital sign condition is detected; and enabling voice communication between said user and said central facility.

17. The method of claim 16, further comprising the step of transmitting ground position information to said central facility.

18. The method of claim 16, wherein said vital signs are selected from the group consisting of body temperature, respiration, oxymetry data, electrocardiogram data, and combinations thereof.

19. The method of claim 16, wherein said sensing step further comprises placing a sensor in engagement with the skin of the chest of the user just below the pectoral muscles.

* * * * *